United States Patent
Trollsas et al.

(10) Patent No.: US 9,629,944 B2
(45) Date of Patent: *Apr. 25, 2017

(54) IMPLANTABLE DEVICE WITH A TRIBLOCK POLYMER COATING

(71) Applicant: ABBOTT CARDIOVASCULAR SYSTEMS INC., Santa Clara, CA (US)

(72) Inventors: O. Mikael Trollsas, San Jose, CA (US); Michael H. Ngo, San Jose, CA (US); David J. Sherman, Tarzana, CA (US); Syed F. A. Hossainy, Hayward, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/160,999

(22) Filed: May 20, 2016

(65) Prior Publication Data
US 2016/0263291 A1 Sep. 15, 2016

Related U.S. Application Data

(63) Continuation of application No. 14/542,983, filed on Nov. 17, 2014, now Pat. No. 9,345,668, which is a
(Continued)

(51) Int. Cl.
*A61F 2/00* (2006.01)
*A61L 31/16* (2006.01)
(Continued)

(52) U.S. Cl.
CPC .......... *A61L 31/10* (2013.01); *A61K 9/5031* (2013.01); *A61K 9/5089* (2013.01); *A61K 31/33* (2013.01); *A61K 31/436* (2013.01); *A61K 31/497* (2013.01); *A61K 31/56* (2013.01); *A61K 38/13* (2013.01); *A61K 38/446* (2013.01); *A61K 45/06* (2013.01); *A61K 47/34* (2013.01); *A61L 27/34* (2013.01); *A61L 31/148* (2013.01); *A61L 31/16* (2013.01); *A61L 2300/416* (2013.01);
(Continued)

(58) Field of Classification Search
CPC .......... A61L 31/10; A61L 31/16; A61L 31/56; A61L 27/34; A61K 38/13; A61K 38/446
See application file for complete search history.

(56) References Cited

U.S. PATENT DOCUMENTS

| 4,826,689 | A | 5/1989 | Volanto |
| 5,145,684 | A | 9/1992 | Liversidge et al. |

(Continued)

FOREIGN PATENT DOCUMENTS

| CA | 2615243 | 2/2014 |
| EP | 1 891 993 | 2/2008 |

(Continued)

OTHER PUBLICATIONS

International Search Report for PCT/US2008/081209, mailed Feb. 23, 2010, 14 pages.
(Continued)

*Primary Examiner* — Lakshmi Channavajjala
(74) *Attorney, Agent, or Firm* — Squire Patton Boggs (US) LLP

(57) ABSTRACT

The present invention provides an implantable device having a coating including a slow dissolving polymer or material and the methods of making and using the same.

20 Claims, 4 Drawing Sheets

Everolimus Elution Profile

Related U.S. Application Data continuation of application No. 14/152,867, filed on Jan. 10, 2014, now Pat. No. 8,889,170, which is a continuation of application No. 11/933,017, filed on Oct. 31, 2007, now Pat. No. 8,642,062.

(51) Int. Cl.

| | | |
|---|---|---|
| *A61L 27/34* | (2006.01) | |
| *A61L 31/10* | (2006.01) | |
| *A61K 31/33* | (2006.01) | |
| *A61K 31/497* | (2006.01) | |
| *A61K 31/56* | (2006.01) | |
| *A61K 38/13* | (2006.01) | |
| *A61K 38/44* | (2006.01) | |
| *A61K 45/06* | (2006.01) | |
| *A61K 47/34* | (2017.01) | |
| *A61K 9/50* | (2006.01) | |
| *A61K 31/436* | (2006.01) | |
| *A61L 31/14* | (2006.01) | |

(52) U.S. Cl.
CPC ... *A61L 2300/602* (2013.01); *A61L 2300/606* (2013.01); *A61L 2420/02* (2013.01)

(56) References Cited

U.S. PATENT DOCUMENTS

| | | |
|---|---|---|
| 5,272,012 A | 12/1993 | Opolski |
| 5,298,262 A | 3/1994 | Na et al. |
| 5,302,401 A | 4/1994 | Liversidge et al. |
| 5,336,507 A | 8/1994 | Na et al. |
| 5,340,564 A | 8/1994 | Illig et al. |
| 5,342,621 A | 8/1994 | Eury |
| 5,346,702 A | 9/1994 | Na et al. |
| 5,352,459 A | 10/1994 | Hollister et al. |
| 5,352,515 A | 10/1994 | Jarrett et al. |
| 5,354,560 A | 10/1994 | Lovrecich |
| 5,384,124 A | 1/1995 | Courteille et al. |
| 5,429,824 A | 7/1995 | June |
| 5,503,723 A | 4/1996 | Ruddy et al. |
| 5,510,118 A | 4/1996 | Bosch et al. |
| 5,518,187 A | 5/1996 | Bruno et al. |
| 5,518,738 A | 5/1996 | Eickhoff et al. |
| 5,534,270 A | 7/1996 | De Castro |
| 5,536,508 A | 7/1996 | Canal et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,662,883 A | 9/1997 | Bagchi et al. |
| 5,662,938 A | 9/1997 | Vert et al. |
| 5,665,331 A | 9/1997 | Bagchi et al. |
| 5,702,717 A | 12/1997 | Cha et al. |
| 5,702,754 A | 12/1997 | Zhong |
| 5,718,919 A | 2/1998 | Ruddy et al. |
| 5,747,001 A | 5/1998 | Wiedmann et al. |
| 5,997,517 A | 12/1999 | Whitbourne |
| 6,001,117 A | 12/1999 | Huxel et al. |
| 6,045,829 A | 4/2000 | Liversidge et al. |
| 6,110,483 A | 8/2000 | Whitbourne et al. |
| 6,117,949 A | 9/2000 | Rathi et al. |
| 6,180,136 B1 | 1/2001 | Larson et al. |
| 6,201,072 B1 | 3/2001 | Rathi et al. |
| 6,274,164 B1 | 8/2001 | Novich |
| 6,306,176 B1 | 10/2001 | Whitbourne |
| 6,494,862 B1 | 12/2002 | Ray et al. |
| 6,503,538 B1 | 1/2003 | Chu et al. |
| 6,544,223 B1 | 4/2003 | Kokish |
| 6,544,543 B1 | 4/2003 | Buchko et al. |
| 6,576,264 B1 | 6/2003 | Henriksen et al. |
| 6,656,216 B1 | 12/2003 | Hossainy |
| 6,656,506 B1 | 12/2003 | Wu et al. |
| 6,663,662 B2 | 12/2003 | Pacetti et al. |
| 6,663,880 B1 | 12/2003 | Roorda et al. |
| 6,673,154 B1 | 1/2004 | Pacetti et al. |
| 6,689,350 B2 | 2/2004 | Uhrich et al. |
| 6,703,040 B2 | 3/2004 | Katsarava |
| 6,712,845 B2 | 3/2004 | Hossainy |
| 6,743,462 B1 | 6/2004 | Pacetti |
| 6,753,071 B1 | 6/2004 | Pacetti |
| 6,758,859 B1 | 7/2004 | Dang et al. |
| 6,780,424 B2 | 8/2004 | Claude |
| 6,790,228 B2 | 9/2004 | Hossainy |
| 6,818,063 B1 | 11/2004 | Kerrigan |
| 6,824,559 B2 | 11/2004 | Michal |
| 6,841,617 B2 | 1/2005 | Jeong et al. |
| 6,916,788 B2 | 7/2005 | Seo et al. |
| 6,926,919 B1 | 8/2005 | Hossainy et al. |
| 6,939,376 B2 | 9/2005 | Shulze et al. |
| 6,972,054 B2 | 12/2005 | Kerrigan |
| 7,005,137 B1 | 2/2006 | Hossainy et al. |
| 7,008,642 B1 | 3/2006 | Roorda et al. |
| 7,022,334 B1 | 4/2006 | Ding |
| 7,056,591 B1 | 6/2006 | Pacetti et al. |
| 7,060,093 B2 | 6/2006 | Dang |
| 7,074,276 B1 | 7/2006 | Van Sciver et al. |
| 7,115,300 B1 | 10/2006 | Hossainy et al. |
| 7,135,038 B1 | 11/2006 | Limon |
| 7,153,520 B2 | 12/2006 | Seo et al. |
| 7,166,680 B2 | 1/2007 | Desnoyer |
| 7,169,178 B1 | 1/2007 | Santos et al. |
| 7,175,874 B1 | 2/2007 | Pacetti |
| 7,195,640 B2 | 3/2007 | Falotico et al. |
| 7,201,935 B1 | 4/2007 | Claude et al. |
| 7,202,325 B2 | 4/2007 | Hossainy |
| 7,217,426 B1 | 5/2007 | Hossainy |
| 7,232,490 B1 | 6/2007 | Hossainy |
| 7,232,573 B1 | 6/2007 | Ding |
| 7,244,443 B2 | 7/2007 | Pacetti |
| 7,247,313 B2 | 7/2007 | Roorda et al. |
| 7,255,891 B1 | 8/2007 | Pacetti |
| 7,261,946 B2 | 8/2007 | Claude |
| 7,288,609 B1 | 10/2007 | Pacetti |
| 7,294,329 B1 | 11/2007 | Ding |
| 7,311,980 B1 | 12/2007 | Hossainy et al. |
| 7,323,209 B1 | 1/2008 | Esbeck et al. |
| 7,329,413 B1 | 2/2008 | Pacetti |
| 7,335,265 B1 | 2/2008 | Hossainy |
| 7,335,391 B1 | 2/2008 | Pacetti |
| 7,341,630 B1 | 3/2008 | Pacetti |
| 7,537,607 B2 | 5/2009 | Gerberding |
| 7,807,211 B2 | 10/2010 | Hossainy et al. |
| 7,951,194 B2 | 5/2011 | Gueriguian et al. |
| 8,017,237 B2 | 9/2011 | Ludwig et al. |
| 8,048,448 B2 | 11/2011 | Ludwig |
| 8,057,824 B2 | 11/2011 | Roorda et al. |
| 8,293,277 B2 | 10/2012 | Swanson et al. |
| 8,372,427 B2 | 2/2013 | Ludwig et al. |
| 8,481,651 B2 | 7/2013 | Hissink et al. |
| 8,512,737 B1 | 8/2013 | Consigny et al. |
| 8,597,673 B2 | 12/2013 | Trollsas et al. |
| 8,603,530 B2 | 12/2013 | Ludwig et al. |
| 8,617,613 B2 | 12/2013 | Wright et al. |
| 8,642,062 B2 | 2/2014 | Trollsas et al. |
| 8,709,472 B1 | 4/2014 | Murase et al. |
| 8,709,473 B1 | 4/2014 | Davalian et al. |
| 8,765,162 B2 | 7/2014 | Ngo et al. |
| 8,877,223 B2 | 11/2014 | Vange et al. |
| 8,889,170 B2 | 11/2014 | Trollsas et al. |
| 8,889,430 B2 | 11/2014 | Yang et al. |
| 8,895,056 B2 | 11/2014 | Pacetti et al. |
| 8,911,766 B2 | 12/2014 | Hossainy et al. |
| 9,044,385 B2 | 6/2015 | Pacetti et al. |
| 9,259,398 B1 | 2/2016 | Klein et al. |
| 9,345,668 B2 | 5/2016 | Trollsas et al. |
| 2001/0007083 A1 | 7/2001 | Roorda |

(56) References Cited

U.S. PATENT DOCUMENTS

| | | |
|---|---|---|
| 2002/0173586 A1 | 11/2002 | Jeong et al. |
| 2003/0073609 A1 | 4/2003 | Pinkerton et al. |
| 2003/0073961 A1 | 4/2003 | Happ |
| 2003/0104028 A1 | 6/2003 | Hossainy et al. |
| 2003/0105518 A1 | 6/2003 | Dutta |
| 2003/0158517 A1 | 8/2003 | Kokish |
| 2003/0190406 A1 | 10/2003 | Hossainy et al. |
| 2004/0001872 A1 | 1/2004 | Shih et al. |
| 2004/0047980 A1 | 3/2004 | Pacetti |
| 2004/0052858 A1 | 3/2004 | Wu et al. |
| 2004/0054104 A1 | 3/2004 | Pacetti |
| 2004/0060508 A1 | 4/2004 | Pacetti |
| 2004/0062853 A1 | 4/2004 | Pacetti et al. |
| 2004/0063805 A1 | 4/2004 | Hossainy |
| 2004/0071861 A1 | 4/2004 | Mandrusov |
| 2004/0072922 A1 | 4/2004 | Hossainy |
| 2004/0073298 A1 | 4/2004 | Hossainy |
| 2004/0086542 A1 | 5/2004 | Hossainy |
| 2004/0106987 A1 | 6/2004 | Palasis et al. |
| 2004/0142015 A1 | 7/2004 | Hossainy et al. |
| 2004/0162609 A1 | 8/2004 | Hossainy et al. |
| 2004/0180132 A1 | 9/2004 | Pacetti |
| 2004/0182312 A1 | 9/2004 | Pacetti et al. |
| 2004/0191405 A1 | 9/2004 | Kerrigan |
| 2004/0199241 A1 | 10/2004 | Gravett et al. |
| 2004/0253203 A1 | 12/2004 | Hossainy |
| 2005/0020734 A1 | 1/2005 | Asgarzadeh et al. |
| 2005/0021127 A1 | 1/2005 | Kawula |
| 2005/0025799 A1 | 2/2005 | Hossainy |
| 2005/0074544 A1 | 4/2005 | Pacetti et al. |
| 2005/0112170 A1 | 5/2005 | Hossainy et al. |
| 2005/0112171 A1 | 5/2005 | Tang et al. |
| 2005/0118344 A1 | 6/2005 | Pacetti |
| 2005/0137381 A1 | 6/2005 | Pacetti |
| 2005/0147647 A1 | 7/2005 | Galuser et al. |
| 2005/0169957 A1 | 8/2005 | Hossainy |
| 2005/0175666 A1 | 8/2005 | Ding |
| 2005/0186261 A1 | 8/2005 | Avelar et al. |
| 2005/0208091 A1 | 9/2005 | Pacetti |
| 2005/0214339 A1 | 9/2005 | Tang et al. |
| 2005/0226991 A1 | 10/2005 | Hossainy et al. |
| 2005/0233062 A1 | 10/2005 | Hossainy et al. |
| 2005/0244363 A1 | 11/2005 | Hossainy et al. |
| 2005/0265960 A1 | 12/2005 | Pacetti et al. |
| 2005/0271700 A1 | 12/2005 | Desnoyer et al. |
| 2005/0287184 A1 | 12/2005 | Hossainy et al. |
| 2006/0002968 A1 | 1/2006 | Stewart et al. |
| 2006/0034888 A1 | 2/2006 | Pacetti et al. |
| 2006/0035854 A1 | 2/2006 | Goldstein et al. |
| 2006/0043650 A1 | 3/2006 | Hossainy et al. |
| 2006/0047336 A1 | 3/2006 | Gale et al. |
| 2006/0062824 A1 | 3/2006 | Pacetti et al. |
| 2006/0089485 A1 | 4/2006 | Desnoyer et al. |
| 2006/0095122 A1 | 5/2006 | Pacetti |
| 2006/0115449 A1 | 6/2006 | Pacetti |
| 2006/0134165 A1 | 6/2006 | Pacetti |
| 2006/0136048 A1 | 6/2006 | Pacetti et al. |
| 2006/0188543 A1 | 8/2006 | Feng |
| 2006/0246108 A1 | 11/2006 | Pacetti et al. |
| 2007/0026043 A1 | 2/2007 | Guan et al. |
| 2007/0032853 A1 | 2/2007 | Hossainy et al. |
| 2007/0055364 A1 | 3/2007 | Hossainy et al. |
| 2007/0141112 A1 | 6/2007 | Falotico et al. |
| 2007/0148251 A1 | 6/2007 | Hossainy et al. |
| 2007/0155906 A1 | 7/2007 | Hissink et al. |
| 2007/0233219 A1 | 10/2007 | Shafi et al. |
| 2007/0258903 A1 | 11/2007 | Kleiner et al. |
| 2008/0008739 A1 | 1/2008 | Hossainy et al. |
| 2008/0051872 A1 | 2/2008 | Borck |
| 2008/0107704 A1 | 5/2008 | Guo |
| 2008/0147175 A1 | 6/2008 | Krivoruchko et al. |
| 2008/0175882 A1 | 7/2008 | Trollsas et al. |
| 2008/0243228 A1 | 10/2008 | Wang et al. |
| 2008/0248098 A1 | 10/2008 | Jin et al. |
| 2008/0306584 A1 | 12/2008 | Kramer-Brown et al. |
| 2009/0004243 A1 | 1/2009 | Pacetti et al. |
| 2009/0047318 A1 | 2/2009 | Ludwig et al. |
| 2009/0047322 A1 | 2/2009 | Vange et al. |
| 2009/0110711 A1 | 4/2009 | Trollsas et al. |
| 2009/0110713 A1 | 4/2009 | Lim et al. |
| 2009/0263457 A1 | 10/2009 | Trollsas et al. |
| 2009/0285873 A1 | 11/2009 | Lim et al. |
| 2009/0297578 A1 | 12/2009 | Trollsas et al. |
| 2009/0297584 A1 | 12/2009 | Lim et al. |
| 2009/0297621 A1 | 12/2009 | Lim et al. |
| 2010/0063585 A1 | 3/2010 | Hoffmann et al. |
| 2011/0027188 A1 | 2/2011 | Kleiner et al. |
| 2015/0174300 A1 | 6/2015 | Trollsas et al. |

FOREIGN PATENT DOCUMENTS

| | | |
|---|---|---|
| JP | 6-41310 A | 2/1994 |
| JP | 2004-000559 | 1/2004 |
| JP | 2004-505063 | 2/2004 |
| JP | 2002-516910 | 2/2006 |
| JP | 2006-512945 | 4/2006 |
| JP | 2007-190369 | 2/2007 |
| JP | 2007-519756 | 7/2007 |
| JP | 2007-522274 | 8/2007 |
| JP | 2007-532640 | 11/2007 |
| WO | WO 99/18142 | 4/1999 |
| WO | WO 02/09768 A2 | 2/2002 |
| WO | WO 2005/000939 | 1/2005 |
| WO | WO 2005/051449 | 6/2005 |
| WO | WO 2006/026201 | 3/2006 |
| WO | WO 2007/009919 | 1/2007 |
| WO | WO 2007/101443 | 9/2007 |
| WO | WO 2007/109069 | 9/2007 |
| WO | WO 2009/129503 | 10/2009 |

OTHER PUBLICATIONS

Japanese Notice of Reasons for Rejection and the translation for appl. No. P2011-505243, dispatched Jul. 2, 2013, 10 pages.

Translation of Japanese Notice of Reasons for Rejection for appl. No. P2010-531295, dispatched Jan. 15, 2013, 3 pages.

Astete et al., Synthesis and characterization of PLGA nanoparticles (2006) *J. Biomater. Sci. Polymer Edn* 17:247-289.

Cai et al., Synthesis and Characterization of Polycaprolactone (B)-Poly(lactide-co-glycolide) (A) ABA Block Copolymer (2000) *Polym. Adv. Technol.* 11:159-166.

Jain R., The manufacturing techniques of various drug loaded biodegradable poly(lactide-co-glycolide) (PLGA) devices (2000) *Biomaterials* 21:2475-2490.

Jeong et al., Drug release from biodegradable injectable thermosensitive hydrogel of PEG-PLGA-PEG triblock polymers (2000) *Journal of Controlled Release* 63:155-163.

Nair et al., Polymers as Biomaterials for Tissue Engineering and Controlled Drug Delivery (2006) *Adv. Biochem.Engin. Biotechnology* 102:47-90.

Sawhney et al., Rapidly degraded terpolymers of dl-lactide, glycolide, and ϵ-caprolactone with increased hydrophilicity by copolymerization with polyethers (1990) 24:1397-1411.

Tollon M., Fabrication of Coated Biodegradable Polymer Scaffolds and Their Effects on Murine Embryonic Stem Cells (2005) University of Florida, 5 pages.

Waksman R., Biodegradable Stents: They Do Their Job and Disappear (2006) *Journal of Invasive Cardiology* 18:1-8.

Japanese Notice of Reasons for Rejection and the translation for appl. No. P2010-531295, dispatched Nov. 5, 2013, 6 pages.

Japanese Final Notice of Reasons for Rejection and the translation for appl. No. P2010-531295, dispatched Aug. 5, 2014, 6 pages.

IMPLANTABLE DEVICE WITH A TRIBLOCK POLYMER COATING

CROSS-REFERENCE TO RELATED APPLICATION

This application is a continuation of U.S. application Ser. No. 14/542,983, filed on Nov. 17, 2014, published as US 2015-0147402 A1 on May 28, 2015, and issued as U.S. Pat. No. 9,345,668 B2 on May 24, 2016; which is a continuation of application Ser. No. 14/152,867, filed on Jan. 10, 2014, published as United States Patent Application Publication number US 2014-0127279 A1 on May 8, 2014, and issued as U.S. Pat. No. 8,889,170 B2 on Nov. 18, 2014; which is a continuation of U.S. application Ser. No. 11/933,017, filed on Oct. 31, 2007, published as United States Patent Application Publication number 2009-0110711 A1 on Apr. 30, 2009, and issued as U.S. Pat. No. 8,642,062 B2 on Feb. 4, 2014; all three of which are incorporated by reference herein in their entirety, including any drawings, and are incorporated by reference herein for all purposes.

FIELD OF THE INVENTION

The present invention relates to a medical device having a dissolvable coating.

BACKGROUND OF THE INVENTION

An ongoing goal of biomaterials research is the improvement of compositions from which medical articles, such as medical devices and coatings for medical devices, are produced. An example of such a medical article is an implantable medical device.

In a variety of medical procedures such as, for example, percutaneous transluminal coronary angioplasty (PTCA), stents play an important role. Stents act as a mechanical intervention to physically hold open and, if desired, expand a passageway within a subject. However, thrombosis and restenosis, which may develop several months after a particular procedure, are among the problems associated with the use of stents and can create a need for additional angioplasty or a surgical by-pass operation.

In order to address these problems, stents are being developed to provide for the local delivery of agents. A method of local delivery includes coating the surface of a medical article, e.g., a stent, with a polymeric carrier and attaching an agent to, or blending it with, the polymeric carrier. These agents can be used alone or in combination with other suitable agents. However, there is a continual need for novel polymer coatings for use on drug delivery devices.

The embodiments described below address the above-identified needs and issues.

SUMMARY OF THE INVENTION

The present invention relates to an implantable device that includes a dissolvable coating or polymeric matrix. Upon implantation, the physiological environment in the implantation site can dissolve away the polymeric matrix via, for example, degradation of the polymer. In some embodiments, the dissolvable coating comprises a poly(D,L-lactide-co-glycolide-b-ethylene glycol-b-D,L-lactide-co-glycolide) triblock copolymer (PLGA-PEG-PLGA) with D,L-lactide/glycolide molar ratio ranging from 5/1 to 3/2 and molar concentration of PEG ranging from 5 to 40 percent.

As used herein, a material that is described as a layer "disposed over" an indicated substrate, e.g., a stent or another layer, refers to a relatively thin coating of the material applied directly to essentially the entire exposed surface of the indicated substrate. The term "disposed over" may, however, also refer to the application of the thin layer of material to an intervening layer that has been applied to the substrate, wherein the material is applied in such a manner that, were the intervening layer not present, the material would cover substantially the entire exposed surface of the substrate. As used herein, the term "polymeric matrix" is used interchangeably with the term "polymeric coating" or "coating."

In some embodiments, the polymeric matrix can include any non-degradable or biodurable polymer or material.

In some embodiments, the polymeric matrix can include a bioactive agent such as a therapeutic substance or drug. Some examples of the bioactive agent include siRNA and/or other oligionucleotides that inhibit endothelial cell migration. The bioactive agent can also be lysophosphatidic acid (LPA) or sphingosine-1-phosphate (S1P). LPA is a "bioactive" phospholipid able to generate growth factor-like activities in a wide variety of normal and malignant cell types. LPA plays an important role in normal physiological processes such as wound healing, and in vascular tone, vascular integrity, or reproduction. Some other exemplary bioactive agents are paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, prodrugs thereof, co-drugs thereof, and combinations thereof.

The polymeric matrix or coating can be formed on an implantable device such as a stent, which can be implanted in a patient to treat, prevent, mitigate, or reduce a vascular medical condition, or to provide a pro-healing effect. Examples of these conditions include atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DETAILED DESCRIPTION

Figure 1A:
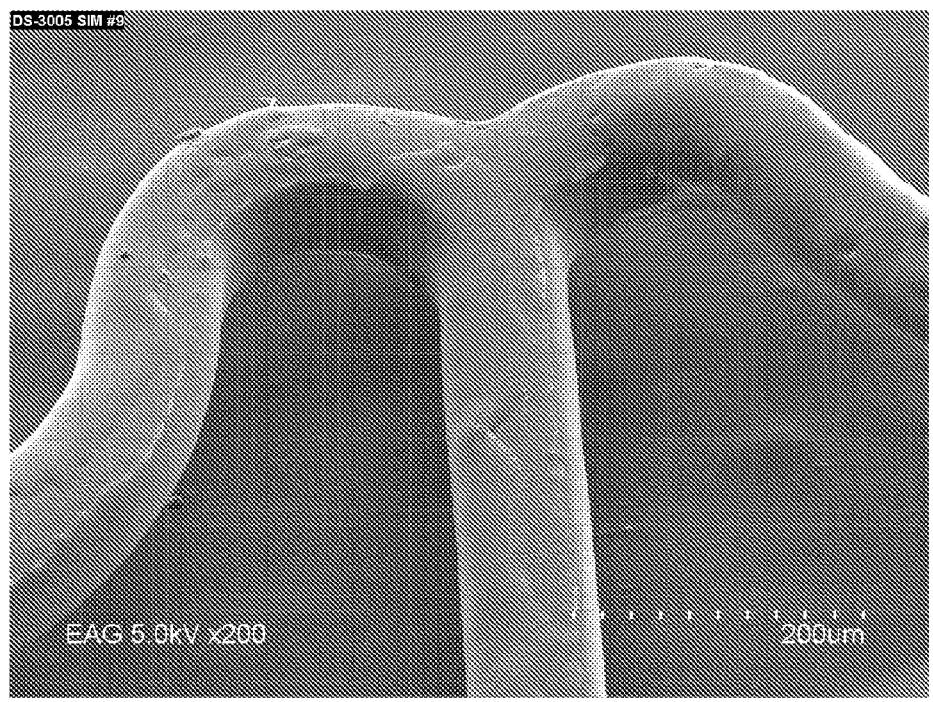
FIGS. 1A-1C are scanning electronic microscopic (SEM) images of coatings formed of polymers of invention PLGA-PEG-PLGA having poly(ethylene glycol) (PEG) in different molecular weights and ratios.

The present invention relates to an implantable device that includes a dissolvable coating or polymeric matrix. Upon implantation, the physiological environment in the implantation site can dissolve away the polymeric matrix via, for example, degradation of the polymer. In some embodiments, the dissolvable coating comprises a poly(D,L-lactide-co-glycolide-b-ethylene glycol-b-D,L-lactide-co-glycolide) triblock copolymer (PLGA-PEG-PLGA) with D,L-lactide/glycolide molar ratio ranging from 5/1 to 3/2 and molar concentration of PEG ranging from 5 to 40 percent.

As used herein, a material that is described as a layer "disposed over" an indicated substrate, e.g., a stent or another layer, refers to a relatively thin coating of the material applied directly to essentially the entire exposed surface of the indicated substrate. The term "disposed over" may, however, also refer to the application of the thin layer of material to an intervening layer that has been applied to the substrate, wherein the material is applied in such a manner that, were the intervening layer not present, the material would cover substantially the entire exposed surface of the substrate. As used herein, the term "polymeric matrix" is used interchangeably with the term "polymeric coating" or "coating."

In some embodiments, the polymeric matrix can include any non-degradable or biodurable polymer or material.

In some embodiments, the polymeric matrix can include a bioactive agent such as a therapeutic substance or drug. Some examples of the bioactive agent include siRNA and/or other oligionucleotides that inhibit endothelial cell migration. The bioactive agent can also be lysophosphatidic acid (LPA) or sphingosine-1-phosphate (S1P). LPA is a "bioactive" phospholipid able to generate growth factor-like activities in a wide variety of normal and malignant cell types. LPA plays an important role in normal physiological processes such as wound healing, and in vascular tone, vascular integrity, or reproduction. Some other exemplary bioactive agents are paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, prodrugs thereof, co-drugs thereof, and combinations thereof.

The polymeric matrix or coating can be formed on an implantable device such as a stent, which can be implanted in a patient to treat, prevent, mitigate, or reduce a vascular medical condition, or to provide a pro-healing effect. Examples of these conditions include atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DEFINITIONS

Wherever applicable, the definitions to some terms used throughout the description of the present invention as provided below shall apply.

As used herein, the term "biostable" is used interchangeably with the term "biodurable". A biostable polymer or coating refers to a polymer or coating that is not biodegradable, which is defined blow.

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 kDa) or less. The process of breaking down and eventual absorption and elimination of the polymer or coating can be caused by, e.g., hydrolysis, metabolic processes, oxidation, enzymatic processes, bulk or surface erosion, and the like. Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal." A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.*, 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.*, 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs*, 29: 455-473 (1985).

The terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked and any other variations thereof.

As used herein, the term "implantable" refers to the attribute of being implantable in a mammal (e.g., a human being or patient) that meets the mechanical, physical, chemical, biological, and pharmacological requirements of a device provided by laws and regulations of a governmental agency (e.g., the U.S. FDA) such that the device is safe and effective for use as indicated by the device. As used herein, an "implantable device" may be any suitable substrate that can be implanted in a human or non-human animal. Examples of implantable devices include, but are not limited to, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages.

As used herein, the term "implantable device" is used interchangeably with the term "medical device."

An implantable device can be designed for the localized delivery of a therapeutic agent. A medicated implantable device may be constructed in part, e.g., by coating the device with a coating material containing a therapeutic agent. The body of the device may also contain a therapeutic agent.

An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

As used herein, a material that is described as a layer or a film (e.g., a coating) "disposed over" an indicated substrate (e.g., an implantable device) refers to, e.g., a coating of the material disposed directly or indirectly over at least a portion of the surface of the substrate. Direct depositing means that the coating is applied directly to the exposed surface of the substrate. Indirect depositing means that the coating is applied to an intervening layer that has been disposed directly or indirectly over the substrate. In some embodiments, the term a "layer" or a "film" excludes a film or a layer formed on a non-implantable device.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

Dissolvable Coating

As used herein, wherein the term "water dissolvable" refers to the attribute of being water soluble of a material or polymer described in this application. This term also encompasses the attribute of a material becoming water soluble if the water includes an ion, which can be an anion or cation. Examples of such ions are, but not limited to, ions present in a physiological environment, e.g., $Na^+$, $K^+$, $Ca^{+2}$, $Mg^{+2}$, $Al^{+3}$, $Cl^-$, $SO_4^{-2}$, or phosphate ions. The term "soluble" refers to the attribute of a material capable of forming a solution having a concentration of the material at least 1 g per 100 cc (or mL) of water at ambient temperature (20° C.).

As used herein, the term "slow dissolving" refers to the attribute of a polymer or material that will not completely dissolve in water or a physiological environment upon contact with water or the physiological environment but rather, will dissolve into a physiological environment over an extended period of time, e.g., one day to up to two years, e.g., a period from about 2 days to about 2 years, from about 4 days to about 20 months, from about 7 days to about 18 months, from about 14 days to about 16 months, from about 30 days to about 14 months, from about 2 months to about 12 months, or about 6 months. In some embodiments, the term "slow dissolving" can be the attribute of a polymeric matrix capable of being dissolved 50 mass % (half life) over a period up to about two years, about one year, about 6 months, about 3 moths, about 2 months, about one months, about 2 weeks, about 1 week, about 2 days, or about 1 day.

In some embodiments, the coating can include a PLGA-PEG-PLGA triblock copolymer. As used herein, the term PLGA is poly(D,L-lactic acid-co-glycolic acid), and PEG is poly(ethylene glycol).

In the PLGA-PEG-PLGA triblock copolymer, the PEG blocks dissolve quickly in an aqueous environment such as a physiological environment and therefore impart dissolvability to the polymer. In addition, the PLGA blocks impart hydrophobicity to the polymer, and the PEG block imparts hydrophilicity to the polymer. Therefore, by varying the concentration of the PEG in the triblock copolymer, one can make a PLGA-PEG-PLGA block polymer having an optimal dissolution rate.

In some embodiments, the PLGA-PEG-PLGA triblock copolymer can be formed of PLGA and PEG blocks with varying molecular weights. Generally, the PEG block can have a weight average molecular weight ($M_w$) below about 40 KD. In some embodiments, the PEG block can have a $M_w$ from about 300 D to about 40 KD. For example, the PEG block can have a $M_w$ of about 500 D, about 1 KD, about 2 KD, about 5 KD, about 8 KD, about 10 KD, about 15 KD, about 20 KD, about 30 KD, about 35 KD, or about 40 KD. As used herein the term "about" refers to a variation within 10% of the indicated value. The PLGA block can have a $M_w$ from about 5 KD to about 100 KD, depending on the desired rate of dissolution. In selecting a proper range of molecular weight for the PLGA block, the following factors are to be considered, among other factors: (1) lactide (LA) units are generally hydrophobic and thus an increase in the percentage of LA units can decrease the water-uptake capacity of the polymer so as to decrease the dissolution rate of the polymer; (2) an increase of the percentage of the PEG block in the polymer will generally increase the water-uptake capacity of the polymer so as to increase the dissolution rate of the polymer; and (3) glycolide (GA) units provide a degradation rate faster than lactide units. In some embodiments, the polymer can have from about 10% to about 90% w/w of the PLGA blocks. In some embodiments, the polymer can have about 20%, about 40%, about 50%, about 60%, about 70%, about 80% or about 90% by weight PLGA blocks. In some embodiments, the polymer can have about 30% by weight the GA units or concentration.

The LA/GA ratio within a PLGA block can also vary. For example, the LA/GA ratio can be from about 5/95, about 10/90, about 20/80, about 30/70, about 40/60, about 50/50, about 60/40, about 70/30, about 80/20, about 90/10, or about 95/5 w/w. Because the difference of rate of dissolution in LA and GA units, a higher ratio of GA in the PLGA will generally generate a PLGA-PEG-PLGA block copolymer with a higher rate of dissolution.

The LA units can be formed of a L-lactic acid (LLA), D-lactic acid (DLA), D,L-lactic acid (DLLA), or meso-lactic acid (mLA). If the LA units are from LLA or DLA, then the PLGA-PEG-PLGA triblock copolymer can be a semi-crystalline polymer. If the LA units are from DLLA, then the PLGA-PEG-PLGA triblock copolymer can be an amorphous polymer. Generally, an amorphous PLGA-PEG-PLGA block copolymer can have a higher dissolution rate, and when used from controlled release of a drug by forming a coating including the drug, the coating can have a release profile of the drug that may include a burst release in the profile. The burst release can be controlled by using a semi-crystalline polymer. A semi-crystalline PLGA-PEG-PLGA triblock copolymer can also have a slower rate of dissolution compared with the amorphous polymer having the same composition.

The PLGA-PEG-PLGA triblock copolymer can have an overall molecular weight ($M_w$) from about 40 KD to about 1000 KD. In some embodiments, the polymer can have an overall $M_w$ from about 50 KD to about 500 KD, e.g., about 60 KD, about 70 KD, about 80 KD, about 90 KD, about 100 KD, about 120 KD, about 130 KD, about 140 KD, about 150 KD, about 160 KD, about 170 KD, about 180 KD, about 190 KD, about 200 KD, about 250 KD, about 300 KD, about 350 KD, about 400 KD, or about 450 KD.

In some embodiments, the polymeric matrix or coating can include a natural polymer such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof.

The coating described herein can be disposed over a substrate that can be the surface of a medical device (e.g., the metallic surface of stent) or a biostable polymeric substrate. The biostable polymeric substrate can include a biostable polymer or material. Such biostable polymeric substrate can include any biostable polymer.

Some examples of such biostable polymers include, but are not limited to, polyesters, co-polyesters, polyethers, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyvinyl ketones, polyvinyl aromatics, such as polystyrene, polyvinyl alcohol (PVOH), polyvinyl esters such a polyvinyl acetate (EVAL), copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, co-polyamides, such as poly ether or ester block amide (PEBAX®), polyoxymethylenes, polyimides, poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), polyalkylene oxides such as poly(ethylene oxide), poly(propylene oxide), polymers and co-polymers of choline or phosphoryl choline bearing monomers, polymers and co-polymers of hydroxyl bearing monomers, such as 2-hydroxyethyl methacrylate (HEMA), hydroxypropyl methacrylate (HPMA), hydroxypropyl methacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), PLURONIC™ surfactants (polypropylene oxide-co-polyethylene glycol), poly(tetramethylene glycol), hydroxy functional poly(vinyl pyrrolidone), or combinations thereof. In some embodiments, the biostable polymer is a polymer or copolymer from fluoro-olefins. Some examples of such polymers are Solef™ polymers, such as poly(vinylidene fluoride) (PVDF) or poly(vinylidene fluoride-co-hexafluoropropene) (PVDF-HFP).

In some embodiments, the copolymer described herein can exclude any one or more of the aforementioned polymers.

Bioactive Agents

These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, or antioxidant properties.

These agents can be cystostatic agents, agents that promote the healing of the endothelium (other than by releasing or generating NO), or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™ (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, clobetasol, corticosteroids or combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

In some embodiments, the bioactive agent that can be included in a coating described herein can specifically exclude any one or more of the above identified drugs or agents.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Implantable Device

As used herein, an implantable device can be any suitable medical substrate that can be implanted in a human or veterinary patient. Examples of such implantable devices include self-expandable stents, balloon-expandable stents, stent-grafts, grafts (e.g., aortic grafts), heart valve prosthesis (e.g., artificial heart valves) or vascular graft, cerebrospinal fluid shunts, pacemaker electrodes, catheters, endocardial leads (e.g., FINELINE® and ENDOTAK,® available from Guidant Corporation, Santa Clara, Calif.), and devices facilitating anastomosis such as anastomotic connectors. The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR 108, cobalt chrome alloy L-605, "MP35N," "MP20N," ELASTINITE® (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device can be, for example, a bioabsorbable stent.

Method of Use

The device (e.g., a stent) described herein is useful for a variety of medical procedures, including, by way of example, treatment of obstructions caused by tumors in the bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guide wire is then advanced through the lesion or proposed site of treatment. Over the guide wire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The following examples are provided to illustrate the various embodiments of the present invention described above and shall not be construed to limit the scope of the present invention.

Coatings formed of PDLGA-PEG-PDLGA with three different compositions were subjected to simulated use tests followed by scanning electronic microscope (SEM) analysis, swelling tests, and drug release profile analysis. The three compositions for the polymer are 70:30 D,L-lactide/glycolide and 13%, 30%, and 40% PEG by mass.

Figure 1B:
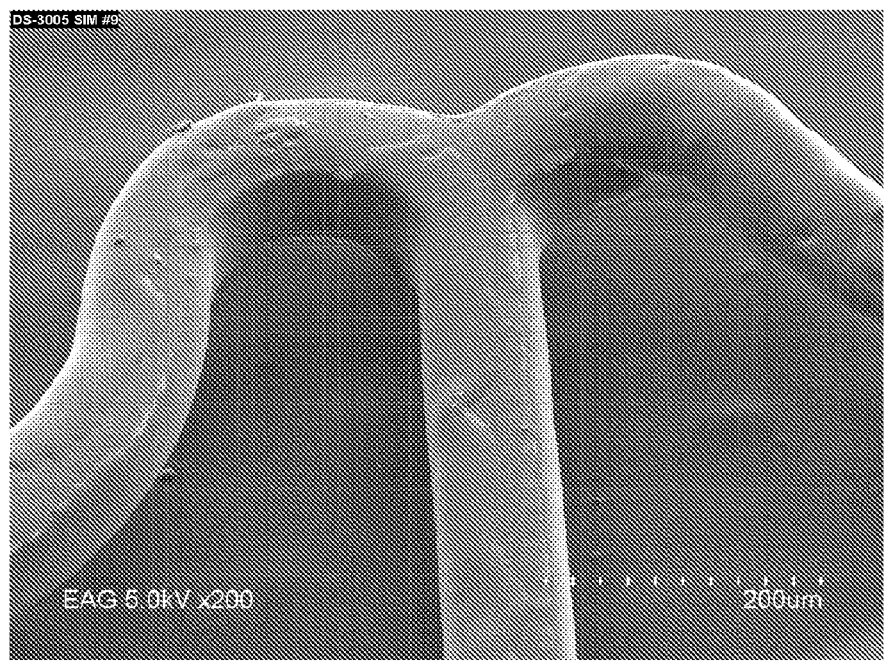
Figure 1C:
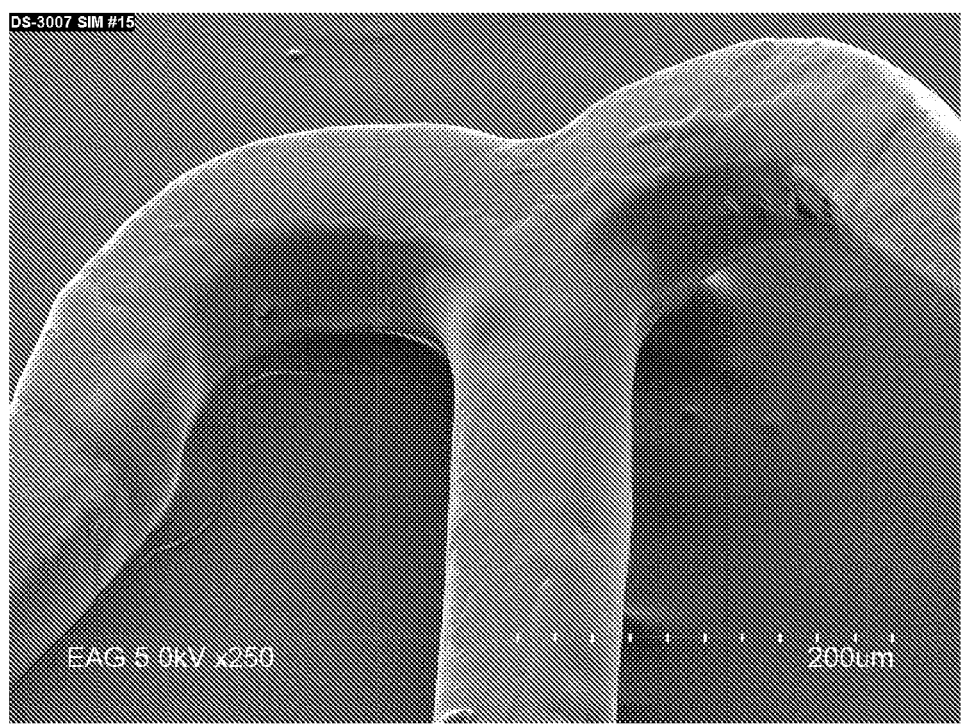

FIG. 1A shows the SEM image of a coating formed of the above polymer with a 10 kD PEG, 13% PEG by mass. FIG. 1B shows the SEM image of a coating formed of the above copolymer with a 20 kD PEG, 30% PEG by mass. FIG. 1C shows the SEM image of a coating formed of the above copolymer with a 20 kD PEG, 40% PEG by mass. The coating formed of the above copolymer with 30% PEG by mass has good coating integrity, and so does the coating formed of the above copolymer with 40% PEG by mass. The coating formed of the above copolymer with 13% PEG by mass shows signs of cracking in high-stress areas, likely because of its relatively low PEG content and relatively low total $M_w$ (79,000 Daltons). There are also signs of dissolution (surface erosion) in the block copolymer with the 20 kD PEG block.

Figure 2:
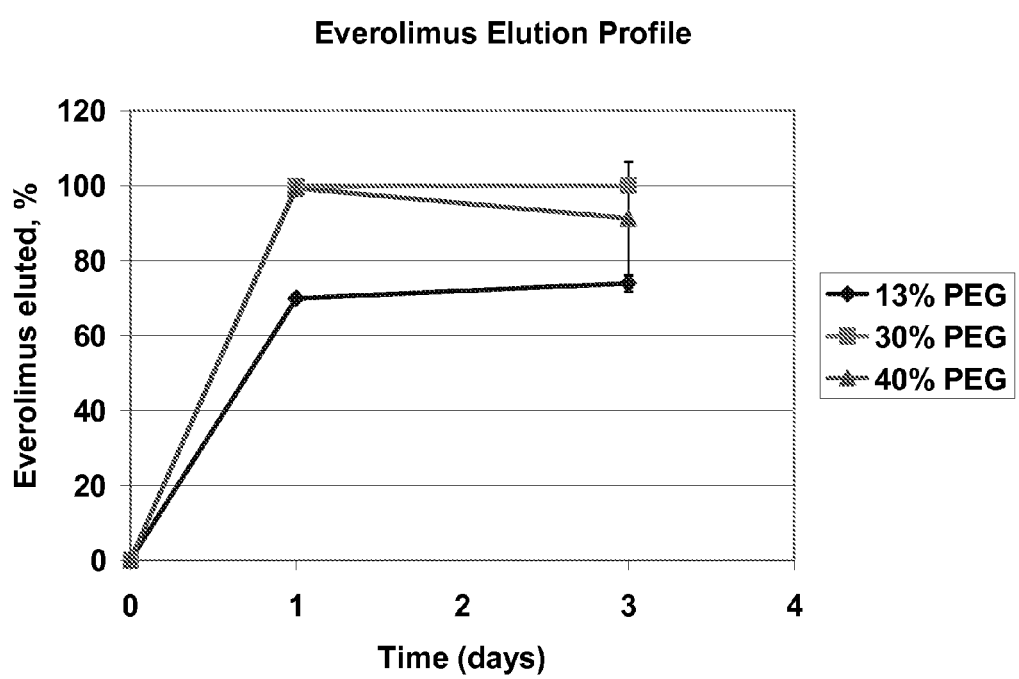
FIG. 2 shows the release profile of everolimus from coatings formed of polymers of invention having PEG in different molecular weights and ratios.

Drug release profile analysis after 1 and 3 days in porcine serum were also conducted. The results are shown in FIG. 2. The coating formed of the polymers with the higher PEG content have burst releases with >99% of the drug released after one day. The coating formed of the polymers with 13% PEG by mass also has a high initial release rate, but the drug release is more controlled than the two with a higher PEG content.

Figure 3:
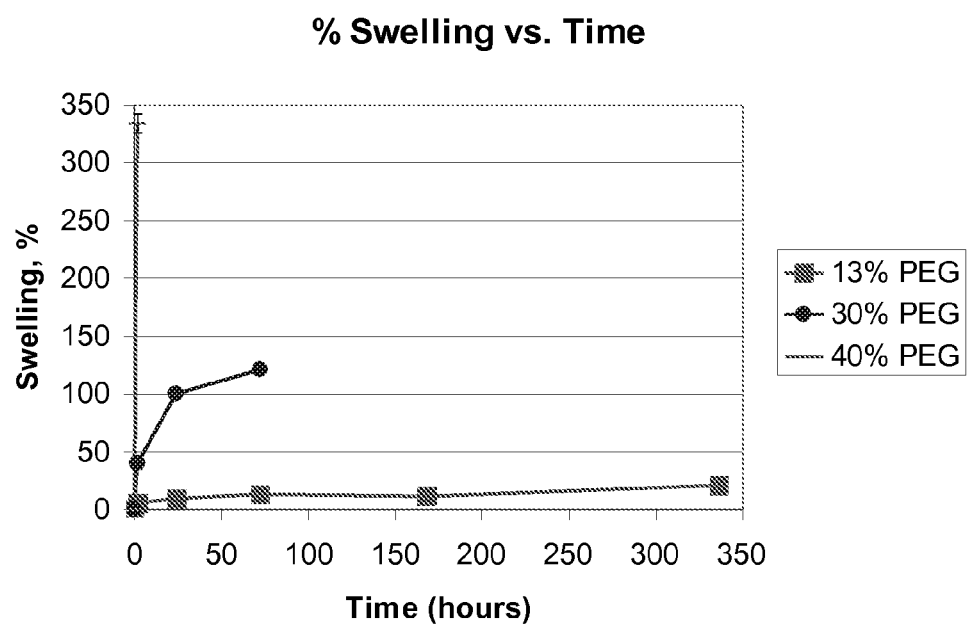
FIG. 3 shows swelling test results of coatings formed of polymers of invention having PEG in different molecular weights and ratios.

Swelling tests of the coatings formed of the above copolymers were performed on these polymers by creating thin films and immersing those films in 37° C. phosphate buffer solution for certain periods of time. The swelling results are shown below in FIG. 3. The large amount of swelling in the two materials with higher PEG contents explains the burst release for those two materials. Additionally, the films of the 30% PEG and 40% PEG materials were soft and broke into small pieces at the points where their graphs stop (the 40% PEG material broke after 2 hours).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. An implantable device comprising a coating deposited thereon, the coating comprising a PLGA-PEG-PLGA triblock copolymer;
   wherein PLGA in the PLGA-PEG-PLGA triblock copolymer is a block of poly(D,L-lactide-co-glycolide) and PEG in the PLGA-PEG-PLGA triblock copolymer is a block of poly(ethylene glycol);
   and
   wherein the PLGA-PEG-PLGA triblock copolymer has a weight average molecular weight ($M_w$) from about 50 KD to about 200 KD and comprises a content of PEG of about 30% or about 40% by weight.

2. The implantable device of claim 1, wherein the PLGA-PEG-PLGA triblock copolymer has a molecular weight of about 40 KD to about 1000 KD.

3. The implantable device of claim 1, wherein the content of PEG in the PLGA-PEG-PLGA triblock copolymer is about 30% by weight.

4. The implantable device of claim 1, wherein the content of PEG in the PLGA-PEG-PLGA triblock copolymer is about 40% by weight.

5. The implantable device of claim 1, wherein the coating further comprises a bioactive agent.

6. The implantable device of claim 5, wherein the bioactive agent is selected from the group consisting of paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), γ-hiridun, clobetasol, pimecrolimus, imatinib mesylate, midostaurin, feno fibrate, prodrugs thereof, co-drugs thereof, and combinations thereof.

7. The implantable device of claim 1, which is a stent.

8. The implantable device of claim 1, which is a bioabsorbable stent.

9. A method comprising depositing a coating over an implantable device, the coating comprising a PLGA-PEG-PLGA triblock copolymer;
   wherein PLGA in the PLGA-PEG-PLGA triblock copolymer is a block of poly(D,L-lactide-co-glycolide) and PEG in the PLGA-PEG-PLGA triblock copolymer is a block of poly(ethylene glycol);
   and
   wherein the PLGA-PEG-PLGA triblock copolymer has a weight average molecular weight ($M_w$) from about 50 KD to about 200 KD and comprises a content of PEG of about 30% or about 40% by weight.

10. The method of claim 9, wherein the content of PEG in the PLGA-PEG-PLGA triblock copolymer is about 30% by weight.

11. The method of claim 9, wherein the content of PEG in the PLGA-PEG-PLGA triblock copolymer is about 40% by weight.

12. The method of claim 9, which is a stent.

13. The method of claim 9, which is a bioabsorbable stent.

14. A method of treating a disorder in a patient, the method comprising implanting in the patient the implantable device according to claim 1, wherein the disorder is selected from the group consisting of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

15. A method of treating a disorder in a patient, the method comprising implanting in the patient the implantable device according to claim 5, wherein the disorder is selected from the group consisting of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

16. The implantable device of claim 5, wherein the bioactive agent is selected from the group consisting of paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), biolimus, tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy)-ethoxy]ethyl-rapamycin, 40-O-tetrazole-rapamycin, 40-epi-(N1-tetrazolyl)-rapamycin (ABT-578), γ-hiridun, clobetasol, pimecrolimus, imatinib mesylate, midostaurin, feno fibrate, and combinations thereof.

17. The implantable device of claim 5, which is a stent.

18. The implantable device of claim 16, which is a stent.

19. A method of treating a disorder in a patient, the method comprising implanting in the patient the stent according to claim 17, wherein the disorder is selected from the group consisting of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

20. A method of treating a disorder in a patient, the method comprising implanting in the patient the stent according to claim 18, wherein the disorder is selected from the group consisting of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation for vein and artificial grafts, bile duct obstruction, ureter obstruction, tumor obstruction, and combinations thereof.

* * * * *